(12) United States Patent
White (10) Patent No.: US 11,853,373 B2
(45) Date of Patent: Dec. 26, 2023

(54) CROSS CORRELATION OF ONLINE IDENTITIES

(71) Applicant: Federal Data Systems LLC, Columbia, MD (US)

(72) Inventor: Joshua S. White, Ilion, NY (US)

(73) Assignee: Federal Data Systems LLC, Columbia, MD (US)

(*) Notice: Subject to any disclaimer, the term of this patent is extended or adjusted under 35 U.S.C. 154(b) by 13 days.

(21) Appl. No.: 17/329,258

(22) Filed: May 25, 2021

(65) Prior Publication Data

US 2022/0382817 A1 Dec. 1, 2022

(51) Int. Cl.
*G06F 16/28* (2019.01)
*G06F 16/9535* (2019.01)
*G06F 16/9536* (2019.01)
*G06F 16/901* (2019.01)

(52) U.S. Cl.
CPC ........ *G06F 16/9535* (2019.01); *G06F 16/288* (2019.01); *G06F 16/9024* (2019.01); *G06F 16/9536* (2019.01)

(58) Field of Classification Search
CPC . G06F 16/288; G06F 16/3347; G06F 16/9535
See application file for complete search history.

(56) References Cited

U.S. PATENT DOCUMENTS

| | | | |
|---|---|---|---|
| 2011/0179116 A1* | 7/2011 | Solomon | G06Q 30/02 709/204 |
| 2016/0110424 A1* | 4/2016 | Goeppinger | G06F 16/35 707/780 |
| 2016/0371346 A1* | 12/2016 | White | G06F 16/367 |
| 2018/0218309 A1* | 8/2018 | Keen | A61B 5/167 |
| 2021/0142191 A1* | 5/2021 | Faruquie | G06N 20/00 |

OTHER PUBLICATIONS

Schafer, J. (2019). Psychological Narrative Analysis: A Professional Method to Detect Deception in Written and Oral Communications (2nd ed.). Charles C Thomas Publisher, Ltd.
Goga, Oana, et al., "Large-scale Correlation of Accounts Across Social Networks," International Computer Science Institute, Apr. 2013.

(Continued)

*Primary Examiner* — Grace Park
(74) *Attorney, Agent, or Firm* — Faegre Drinker Biddle & Reath LLP (57) ABSTRACT

A method for analyzing social network accounts includes querying a first social network for data about a first user account associated with the first social network. The received data is stored in a social graph structure and used to determine derived characteristics of the first user account. The derived characteristics are quantified and used to generate a first feature vector for the first user account. The first feature vector of the first user account is compared with a second feature vector of a second user account associated with a second social network different from the first social network. Based on the comparison of the first and second feature vectors, it is determined whether the first user account and the second user account are associated with a same entity.

19 Claims, 5 Drawing Sheets

(56) References Cited

OTHER PUBLICATIONS

Gurajala, Supraja, et al., "Fake Twitter accounts: Profile characteristics obtained using an activity-based pattern detection approach," Pending Publication, 2015.

Koppel, Moshe, et al., "Automatically Categorizing Written Texts by Author Gender," Literary and Linguistic Computing, vol. 17, Issue 4, Nov. 2002, pp. 401-412, doi:10.1093/llc/17.4.401 (http://u.cs.biu.ac.il/~koppel/papers/male-female-llc-final.pdf).

White, Joshua S., et al., "It's you on photo?: Automatic Detection of Twitter Accounts Infected With the Blackhole Exploit Kit," IEEE Conference MALWARE 2013, Puerto Rico, DOI: 10.1109/MALWARE.2013.6703685.

* cited by examiner

CROSS CORRELATION OF ONLINE IDENTITIES

TECHNICAL FIELD

The present disclosure relates generally to analyzing online social networks and, more particularly, to identifying social network accounts associated with the same entity.

BACKGROUND

With the proliferation of social media and online communities, it is not uncommon for an individual to have multiple user accounts across different social networking platforms. However, social networks vary in terms of their theme or purpose, functionality, popularity, and accessibility. Given these differences, an individual may choose to present himself or herself in different ways depending on the particular social network. For example, a person or entity may use one user name for a first social network and quite a different user name for a second social network. In addition, the availability of demographic indicators associated with user accounts differs from one social network to the next. For these and other reasons, it is often difficult to determine when multiple social networking accounts are owned by the same individual.

A number of approaches have been developed for comparing user accounts across social networks. One existing approach looks to photograph matching, name similarity, and location similarity to correlate user accounts. Another approach attempts to correlate user accounts utilizing text based entropy of screen names, similarity of profile photos, and time patterns detected in posting activity and account creation. However, where these and other existing approaches fall short is that they fail to take into account that social networks are now broken into distinct subcategories, and each category does not provide the same measurable characteristics as the others.

SUMMARY

The following introduces a selection of concepts in a simplified form in order to provide a foundational understanding of some aspects of the present disclosure. The following is not an extensive overview of the disclosure, and is not intended to identify key or critical elements of the disclosure or to delineate the scope of the disclosure. The following merely provides an overview for some of the concepts of the disclosure as an introduction to the more detailed description provided thereafter.

In an embodiment, a method for analyzing social network accounts includes: querying, using data processing hardware, a first social network for data about a first user account associated with the first social network; receiving, at the data processing hardware, the data about the first user account associated with the first social network; storing, by the data processing hardware, the received data in a social graph structure; determining, by the data processing hardware, derived characteristics of the first user account based on the data stored in the social graph structure; quantifying, by the data processing hardware, the derived characteristics of the first user account; generating, by the data processing hardware, a first feature vector for the first user account based on the quantified characteristics of the first user account; comparing, by the data processing hardware, the first feature vector of the first user account with a second feature vector of a second user account associated with a second social network different from the first social network; and determining, by the data processing hardware, based on the comparison of the first and second feature vectors, whether the first user account and the second user account are associated with a same entity, where the first user account and the second user account are determined to be associated with the same entity when the comparison satisfies a predetermined condition.

According to an embodiment, a system comprises data processing hardware and memory hardware in communication with the data processing hardware and storing instructions that when executed on the data processing hardware cause the data processing hardware to perform operations including: querying a first social network for data about a first user account associated with the first social network; receiving the data about the first user account associated with the first social network; storing the received data in a social graph structure; determining derived characteristics of the first user account based on the data stored in the social graph structure; quantifying the derived characteristics of the first user account; generating a first feature vector for the first user account based on the quantified characteristics of the first user account; comparing the first feature vector of the first user account with a second feature vector of a second user account associated with a second social network different from the first social network; and determining, based on the comparison of the first and second feature vectors, whether the first user account and the second user account are associated with a same entity, where the first user account and the second user account are determined to be associated with the same entity when the comparison satisfies a predetermined condition.

According to another embodiment, a non-transitory computer-readable storage medium includes instructions that, when executed by at least one processor of a computing device, cause the computing device to perform operations comprising: querying a first social network for data about a first user account associated with the first social network; receiving the data about the first user account associated with the first social network; storing the received data in a social graph structure; determining derived characteristics of the first user account based on the data stored in the social graph structure; quantifying the derived characteristics of the first user account; generating a first feature vector for the first user account based on the quantified characteristics of the first user account; comparing the first feature vector of the first user account with a second feature vector of a second user account associated with a second social network different from the first social network; and determining, based on the comparison of the first and second feature vectors, whether the first user account and the second user account are associated with a same entity, where the first user account and the second user account are determined to be associated with the same entity when the comparison satisfies a predetermined condition.

Further scope of applicability of the systems, methods, and apparatus of the present disclosure will become apparent from the more detailed description given below. However, it should be understood that while specific examples indicating embodiments of the systems, methods, and apparatus, are given by way of illustration only, since various changes and modifications within the spirit and scope of the concepts disclosed herein will become apparent to those skilled in the art from the following detailed description.

BRIEF DESCRIPTION OF THE DRAWINGS

Features of the present systems and techniques may be best understood from the following detailed description taken in conjunction with the accompanying drawings of which.

The headings provided herein are for convenience only and do not necessarily affect the scope or meaning of what is claimed in the present disclosure.

Embodiments of the present disclosure and their advantages are best understood by referring to the detailed description that follows. It should be appreciated that like reference numbers are used to identify like elements illustrated in one or more of the figures, wherein showings therein are for purposes of illustrating embodiments of the present disclosure and not for purposes of limiting the same.

DETAILED DESCRIPTION

Various examples and embodiments of the present disclosure will now be described. The following description provides specific details for a thorough understanding and enabling description of these examples. One of ordinary skill in the relevant art will understand, however, that one or more embodiments described herein may be practiced without many of these details. Likewise, one skilled in the relevant art will also understand that one or more embodiments of the present disclosure can include other features and/or functions not described in detail herein. Additionally, some well-known structures or functions may not be shown or described in detail below, so as to avoid unnecessarily obscuring the relevant description. It is originally intended to combine the configurations described in the various embodiments as appropriate. Also, one or more of the components in the embodiments disclosed herein may not be used.

Various embodiments set forth in the present disclosure are directed to a method, system, and computing device that utilizes feature vectors for comparing user accounts across social network platforms. As will be described in greater detail herein, the methods and systems use a graph distance measurement to compare features of different user accounts in order to identify accounts that potentially belong to the same person or entity.

Figure 1:
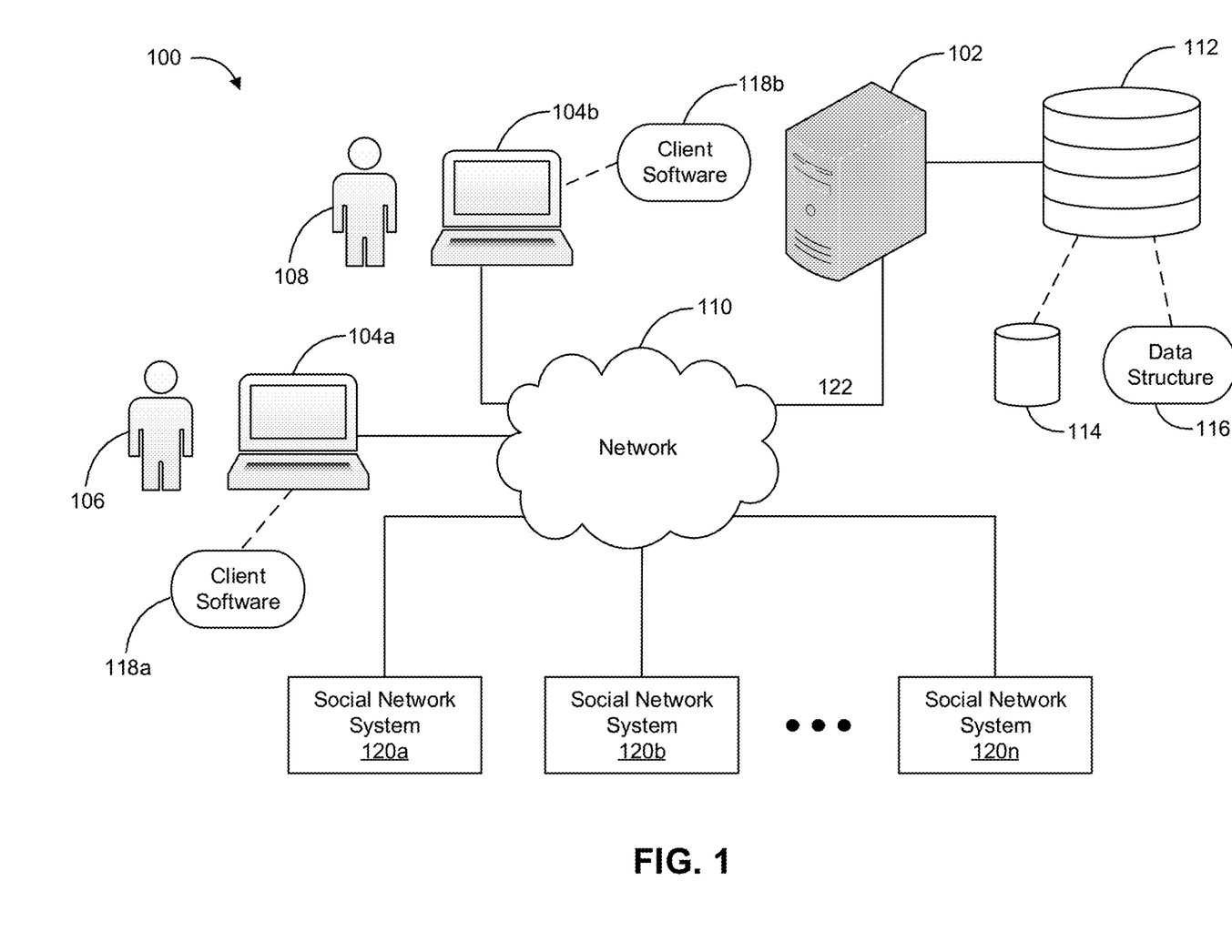
FIG. 1 is an example of a networking environment in which various embodiments of the disclosure may be employed.

Various embodiments of the disclosure are implemented in a computer networking environment. Turning to FIG. 1, an example of such an environment is shown. A first computing device 102 is communicatively linked to a network 110. Possible implementations of the network 110 include a local-area network, a wide-area network, a private network, a public network (e.g., the Internet), or any combination of these. The network 110 may include both wired and wireless components. The first computing device 102 is communicatively linked to a media storage device 112 (e.g., a redundant array of independent disks or other suitable storage medium). In an embodiment, a database 114 may reside within media storage device 112. Also communicatively linked to the network 110 are a second computing device 104a (which may also referred to as a "first client device" or, when there is no specific mention of first computing device 102, the "first computing device") and a third computing device 104b (also referred to as a "second client device" or, when there is no specific mention of first computing device 102, the "second computing device"). For the sake of example, it is assumed that a first user 106 operates second computing device 104a, and a second user 108 operates third computing device 104b. In some instances, the first user 106 and the second user 108 may be the same individual, while in other instances the first user 106 and the second user 108 may be different individuals. In an embodiment, each of computing devices 104a and 104b may execute client software 118a and 118b, respectively. An example implementation of client software 118a, 118b is a web browser. It should be understood that the networking environment may include any number of computing devices (e.g., hundreds of client devices) and the number depicted in FIG. 1 is meant only to be representative.

Also communicatively linked to the network 110 are a plurality of social network systems 120a through 120n (where "n" is an arbitrary number). In an embodiment, each of social network systems 120a through 120n may be a network-addressable computing system that is capable of hosting an online social network. Each social network system 120 may be accessed by computing devices 102, 104a, 104b by any suitable manner (e.g., either directly or via network 110). In one embodiment, each social network system 120 may include one or more servers (not shown) such as, for example, web servers, mail servers, message servers, file servers, application servers, proxy servers, and the like. Each social network system 120 may also include one or more data stores (not shown) that may be used to store various types of information. Such data stores may be relational databases, for example. In an embodiment, each social network system 120 may generate, send, receive, and store social networking data including, for example, user profile data, social graph information, and other suitable data associated with the online social network.

Computing devices 102, 104a, and 104b, and social network systems 120a through 120n may be communicatively connected to network 110 via one or more links 122. While the present disclosure contemplates any suitable links 122, in one or more embodiments, links 122 may be wireless links (e.g., Wi-Fi or Worldwide Interoperability for Microwave Access (WiMAX)), wireline links (e.g., Digital Subscriber Line (DSL) or Data Over Cable Service Interface Specification (DOC SIS)), or optical links (e.g., Synchronous Optical Network (SONET) or Synchronous Digital Hierarchy (SDH)). In some embodiments, one or more of links 122 may each include an intranet, extranet, ad hoc network, VPN, LAN, WLAN, WAN, a portion of the Internet, a cellular technology-based network, another link 122, or any suitable combination of two or more such links 122. Furthermore, each of computing devices 102, 104a, and 104b, and social network systems 120 need not necessarily be connected to network 110 via the same type of link 122.

It should be noted that computing devices 102, 104a, and 104b depicted in FIG. 1 are merely representative. While computing device 102 is depicted as a server and computing devices 104a and 104b are depicted as notebook computers, numerous other implementations of computing devices are also possible. For example, one or both of computing devices 104a and 104b may be a desktop computer, a tablet computer, or a smartphone.

Although FIG. 1 illustrates a particular arrangement of computing devices (e.g., computing devices 102, 104a, and 104b), social network systems (e.g., social network systems 120a through 120n), and network 110, the present disclosure contemplates any suitable arrangement of such computing devices, social network systems, and network. In an exemplary embodiment, and not by way of limitation, two or more of computing devices 102, 104a, and 104b and social network systems 120a through 120n may be connected to each other directly, bypassing network 110.

Figure 2:
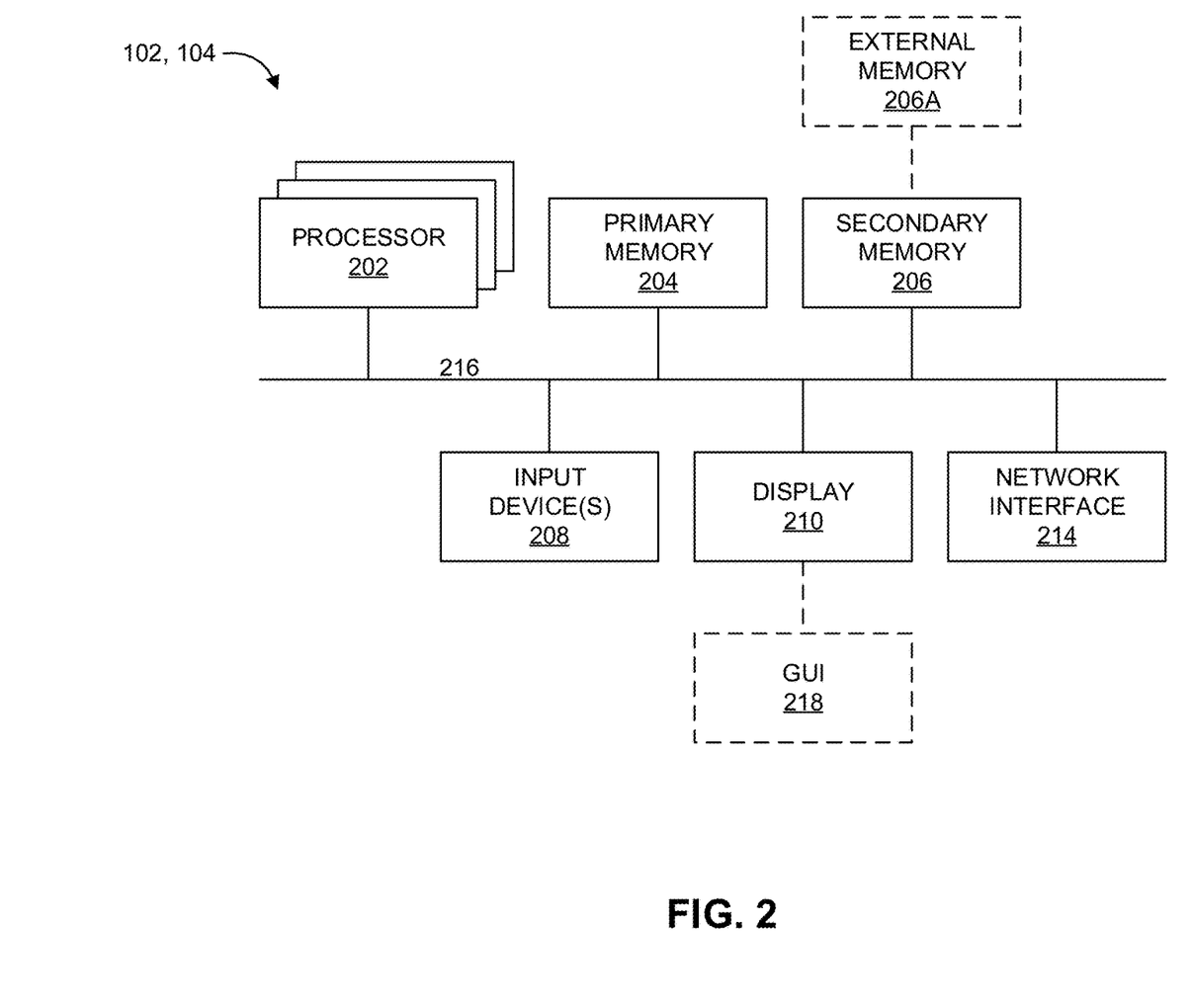
FIG. 2 is a block diagram of a computing device according to an embodiment.

According to an embodiment, one or more of the computing devices of FIG. 1 (including media storage device 112) have the general architecture shown in FIG. 2. The device depicted in FIG. 2 includes one or more processors 202 (e.g., one or more microprocessors, controllers, or application-specific circuit), a primary memory 204 (e.g., volatile memory, random-access memory), a secondary memory 206 (e.g., non-volatile memory), one or more input devices 208 (e.g., keyboard, mouse, or touchscreen), a display (e.g., an organic, light-emitting diode display), and a network interface 212 (which may be wired or wireless). Memories 204 and 206 store instructions and data. The one or more processors 202 execute the instructions and use the data to carry out various procedures including, in some embodiments, the methods described herein.

Each of the elements of FIG. 2 is communicatively linked to one or more other elements via one or more data pathways 216. Possible implementations of the data pathways 216 include wires, conductive pathways on a microchip, and wireless connections. In an embodiment, processor 202 is one of multiple processors in the computing device, each of which is capable of executing a separate thread. In an embodiment, processor 202 communicates with other processors external to the computing device in order to initiate the execution of different threads on those other processors.

As used herein, "local memory" refers to one or both of memories 204 and 206 (i.e., memory accessible by processor 202 within the computing device). In some embodiments, secondary memory 206 is implemented as, or supplemented by an external memory 206A. Media storage device 112 is a possible implementation of external memory 206A. Processor 202 executes the instructions and uses the data to carry out various procedures including, in some embodiments, the methods described herein, including displaying a graphical user interface 218. Graphical user interface 218 is, according to one embodiment, software that processor 202 executes to display a report on display 210, and which permits a user to make inputs into the report via input devices 208.

In the exemplary embodiment of FIG. 1, computing devices 102, 104a, and 104b (e.g., processor 202 of each of the computing devices) are able to communicate with other devices of FIG. 1 via network interface 214 over network 110. In an embodiment, such communication occurs via a user interface that first computing device 102 provides to second computing device 104a and third computing device 104b. The specific nature of the user interface and what the user interface shows at any given time may vary depending what the user (e.g., user 106 or 108) has chosen to view. Also, multiple users may interact with different instances of the user interface on different devices. In some embodiments, first computing device 102 carries out calculations to determine how content is to be rendered on a computing device, generates rendering instructions based on those calculations, and transmits those rendering instructions to the computing device. Using the received instructions, the computing device (e.g., second computing device 104a and/or third computing device 104b) renders the content on a display (e.g., display 210). In other embodiments, first computing device 102 transmits instructions regarding an asset to a computing device. In carrying out the received instructions, the computing device performs the appropriate calculations locally to render the content of the asset on a display.

The following description of examples and embodiments may sometimes refer to one or more of client software 118a, client software 118b, first computing device 102, second computing device 104a, or third computing device 104b as taking one or more actions. It is to be understood that such actions may involve one or both of client software 118a and client software 118b taking such actions as: (a) the client software transmitting hypertext transport protocol commands such as "Get" and "Post" in order to transmit to or receive information from software running on first computing device 102 (e.g., via a web server), and (b) the client software running a script (e.g., JavaScript) to send information to and retrieve information from software running on first computing device 102. First computing device 102 may ultimately obtain information (e.g., web pages or data to feed into plugins used by the client software) from database 114. It should be understood, however, that when a computing device (or software executing thereon) carries out an action, it is processor hardware 202 (the main processor and/or one or more secondary processors, such as a graphics processing unit, hardware codec, input-output controller, etc.) that carries out the action at the hardware level.

In one or more embodiments, media storage device 112 may store data in one or more data structures 116. One possible implementation of data structure 116 is a social graph structure. For example, in an embodiment, first computing device 102 may obtain data about user accounts from one or more of social network systems 120a through 120n. Such data obtained from social network systems 120 may be stored in a social graph structure 116.

Figure 3:
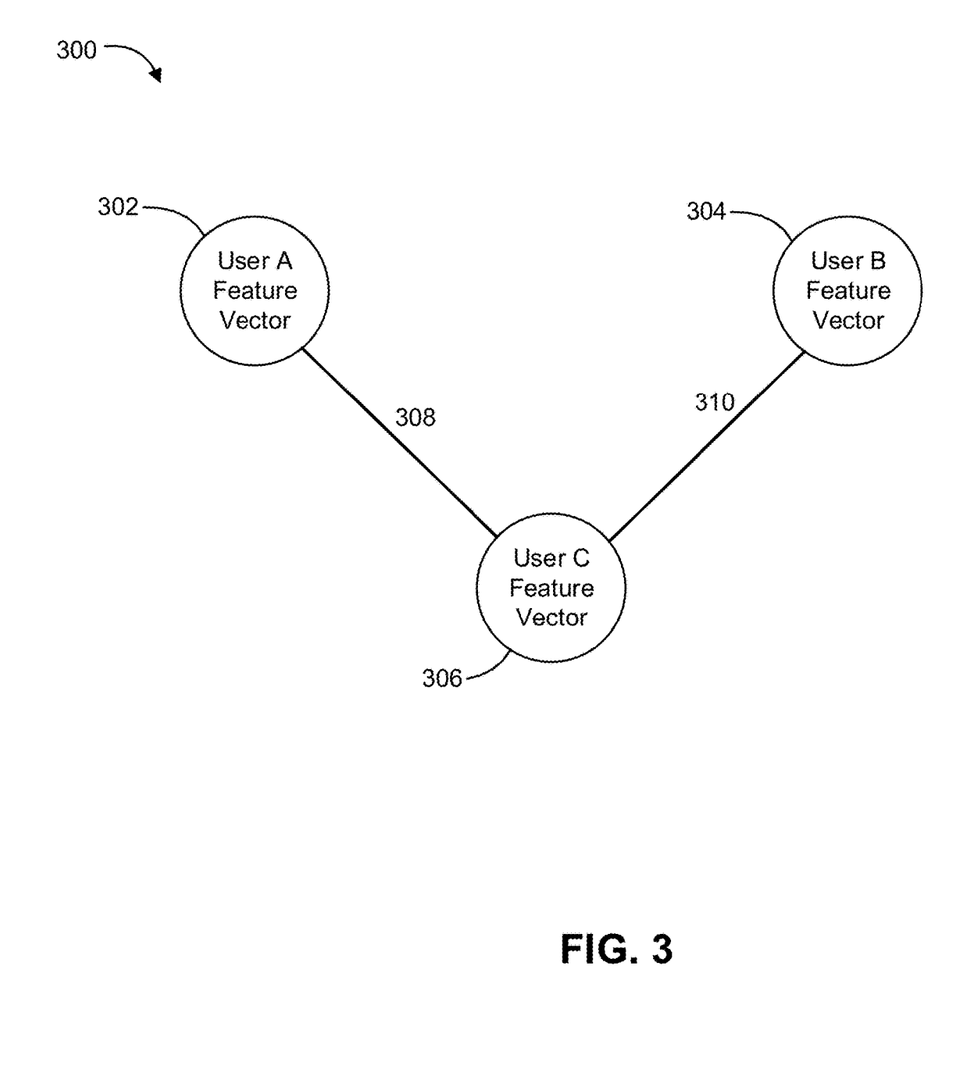
FIG. 3 is a diagram illustrating an example social graph structure, according to an embodiment.

A social graph structure may include multiple nodes and multiple edges connecting the nodes. An example social graph structure 300 is illustrated in FIG. 3. As shown in FIG. 3, in particular embodiments, each node 302, 304, and 306 of the social graph 300 may be comprised of a feature vector, and nodes 302, 304, 306 are connected to one another by edges 308, 310.

Figure 4:
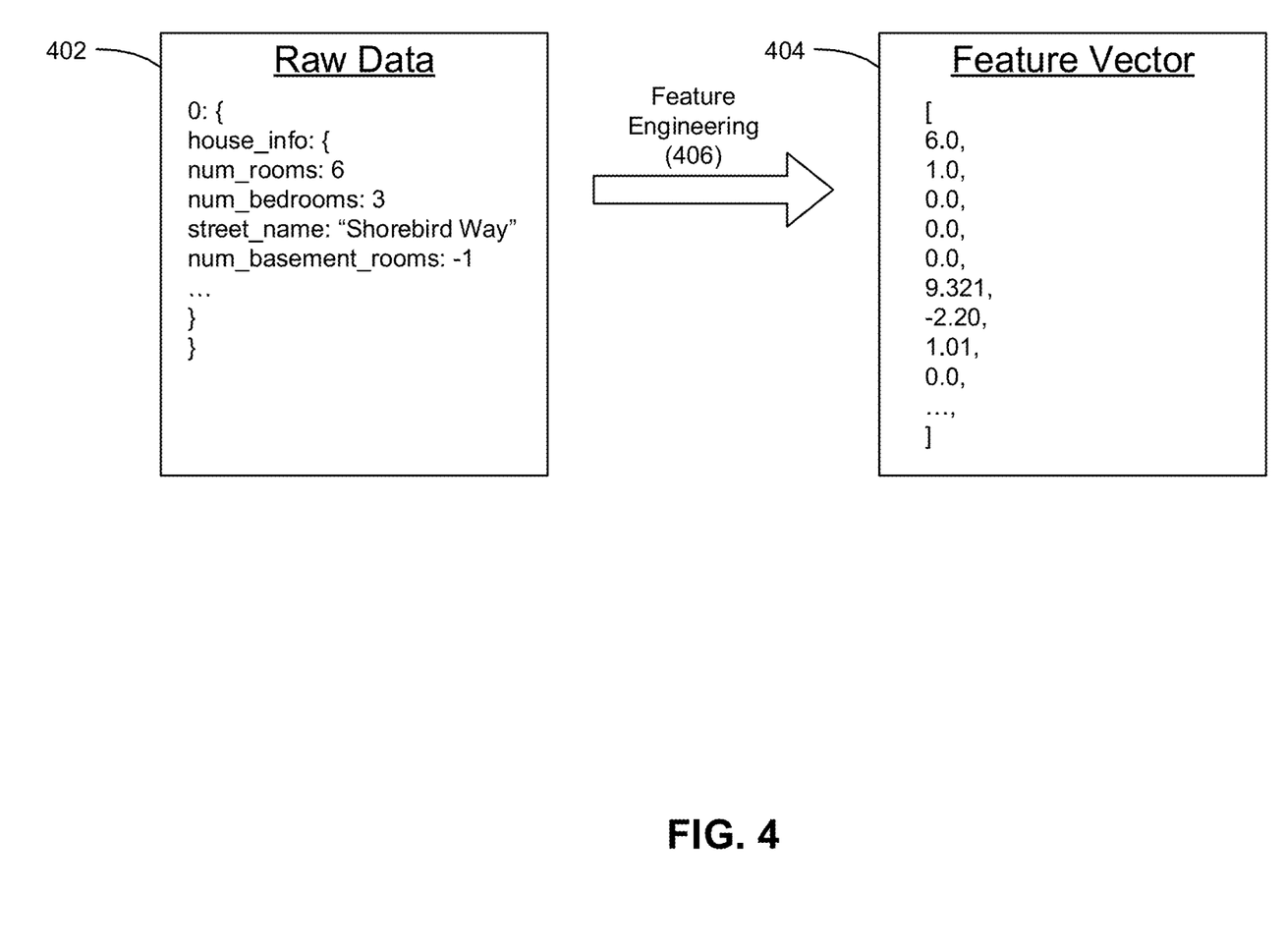
FIG. 4 is a diagram illustrating an example creation of a feature vector, according to an embodiment.

FIG. 4 is a diagram illustrating an example creation of a feature vector, according to an embodiment. In some embodiments, the feature vector is created by first computing device 102 of FIG. 1, through interactions with social network systems 120 and computing devices 104a and 104b. In other embodiments, however, the feature vector may be created by another suitable computing device.

As shown in FIG. 4, a feature vector 404 is created from raw data 402 through a feature engineering process 406. In accordance with at least one embodiment, the feature engineering process 406 may take raw data from a user agent string contained, for example, in a social media post by a user and generate a single feature from that raw data. For example, if a user makes a social media post, then the feature engineering 406 may determine, based on the raw data received about that post, (i) whether a user agent string is present (YES=1, NO=0); (ii) whether the user agent string denotes a device type (YES=1, NO=0); and whether the device type is a PC=0, smartphone=1, smartwatch=2. So if the user's post contains a user agent string that identifies the user is posting from a smartphone, feature engineering 406 would generate a feature of [1,1,1]. In an embodiment, this feature would be combined with other features that are measured about the user (e.g., the user's location, time zone, entropy, etc.) to create a feature vector, which in a simplified form may look like {[1,1,1], [1,0,1], . . . , [1,0,2]}.

Figure 5:
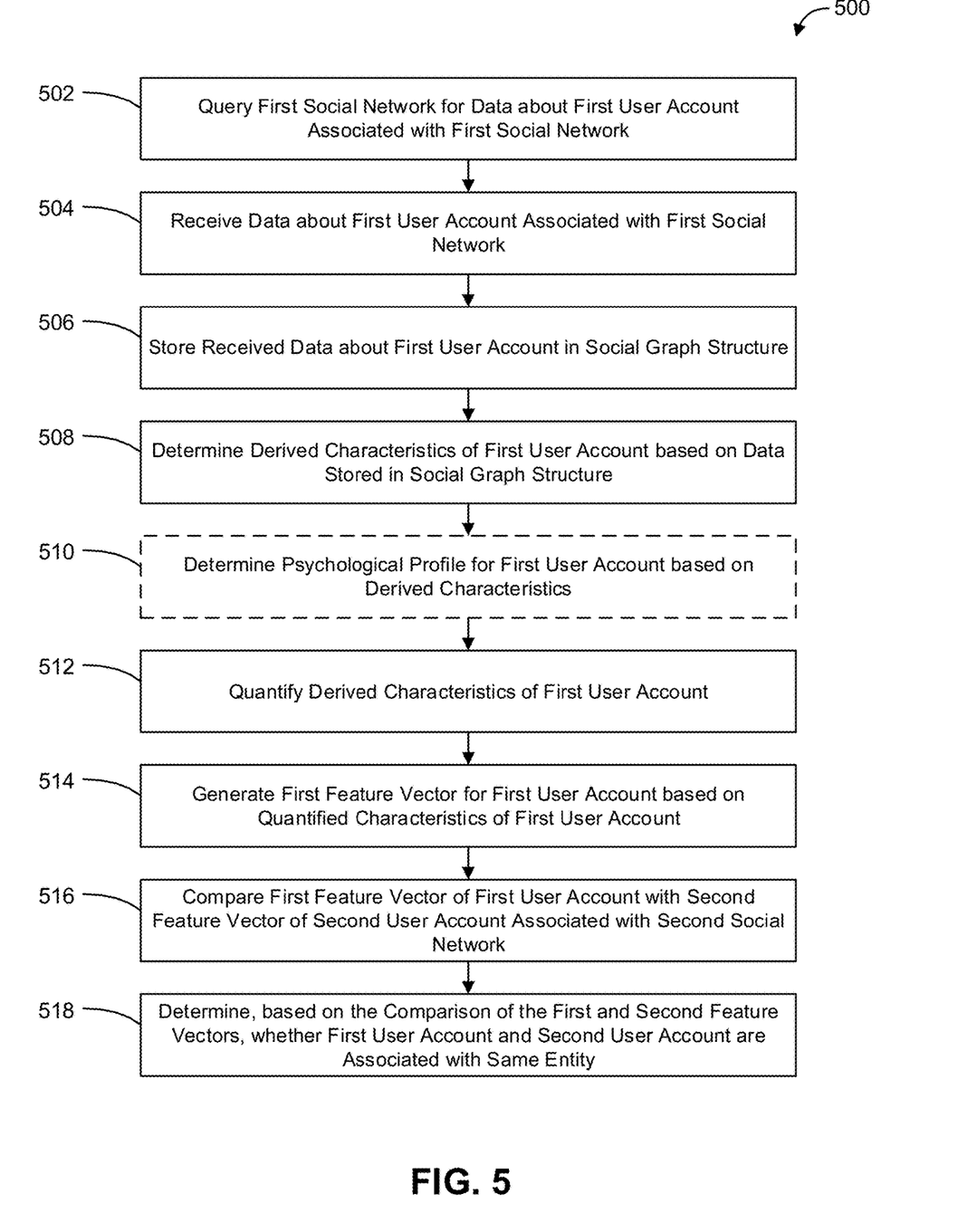
FIG. 5 is a flowchart illustrating an example method for analyzing social network accounts.

FIG. 5 is a flowchart illustrating an example method, implemented by data processing hardware, for analyzing social network accounts, according to an embodiment. In some embodiments, method 500 is implemented by first computing device 102 of FIG. 1, which interacts with social network systems 120 and computing devices 104a and 104b. FIG. 5 is described with reference to FIGS. 1 and 2 for explanatory purposes. In other embodiments, however, method 500 is implemented by another suitable computing device.

At block 502, first computing device 102 queries a first social network (e.g., one of social network systems 120 in FIG. 1) for data about a first user account associated with the first social network. In one embodiment, the query by first computing device 102 may be a search query initiated via an application program interface (API). The query from first computing device 102 to the first social network may be a query for data associated with the activities of the first user account within the social network.

At block 504, first computing device 102 may receive, in response to the query from step 502, data about the first user account associated with the first social network. At block 506, first computing device 102 may store the received data in a social graph structure (e.g., data structure 116 in FIG. 1). For example, in one embodiment, the received data about the first user account may be stored in a social graph structure that is stored in media storage device 112 as a nested JavaScript Object Notation (JSON) Object.

One possible example of the type of data that may be received from the social network and stored in the social graph structure as a nested JSON Object is: Account Username: {"friends:" [list], "followers:" [list], "mentions from:" [list], "mentions at": [list]}. In some embodiments, the data may be formatted slightly different than in this example, and/or additional data about the first user account may be included. For example, the data received by the first computing device at block 502 may include data about the first user account's friends in the social network, followers in the social network, mentions of the first user account by other user accounts, mentions about other user accounts from the first user account, other user accounts who "liked" or reacted to a post by the first user account.

At block 508, first computing device 102 may determine derived characteristics of the first user account based on the data stored in the social graph structure for the first user account. In an embodiment, the derived characteristics determined at block 508 may include, for example, frequency of interaction, average time of interaction, time zone of the access, IP address of the access (e.g., what node on the social network did the first user account access), API of interaction (e.g., API access via web, mobile, direct, etc.), and the like.

At block 510, first computing device 102 determines a psychological profile for the first user account based on the derived characteristics of the first user account determined at block 508. In at least one embodiment, determining a psychological profile for the first user account includes generating (e.g., computing, measuring, etc.) a normalized weighted measurement (e.g., score) for at least one pre-defined personality trait or characteristic. For example, in one embodiment, first computing device 102 may generate a normalized weighted score for at least one of (i) agreeableness, (ii) conscientiousness, (iii) extraversion, (iv) emotional range, and (v) openness of the first user account. In another embodiment, first computing device 102 may generate a normalized weighted score for one or more other personality traits or characteristics in addition to or instead of the example traits discussed above. For example, the particular personality traits that are measured at block 510 may vary depending on a geographical location associated with the first user account.

In some embodiments, the method 500 may be performed without the actions of block 510. For example, in some scenarios there may not be enough data about the first user account to generate normalized measurements of personality traits so as to determine a psychological profile for the first user account. In such instances, the method 500 can proceed without block 510.

At block 512, the derived characteristics of the first user account determined at block 508 are quantified by first computing device 102.

At block 514, first computing device 102 generates a first feature vector for the first user account based on the quantified characteristics (determined at block 512) and, when a psychological profile for the first user account is determined at block 510, the normalized weighted score for the at least one personality trait or characteristic of the first user account. An example of creating a feature vector from raw data is shown in FIG. 4.

At block 516, first computing device 102 compares the first feature vector of the first user account (generated at block 514) with a second feature vector of a second user account associated with a second social network (e.g., one of social network systems 120 in FIG. 1) different from the first social network. In one embodiment, the first feature vector of the first user account is compared to the second feature vector of the second user account by calculating a Hamming distance between the first feature vector and the second feature vector. In another embodiment, the first feature vector and the second feature vector may be compared using another suitable technique. For example, instead of calculating the Hamming distance, the first and second feature vectors may be compared using Cosine Similarity, Minkowski Distance, Manhattan Distance, or Euclidean Distance.

At block 518, first computing device 102 determines, based on the comparison performed at block 516, whether the first user account and the second user account are associated with the same entity. In an embodiment, the determination may be made based on whether a calculated Hamming distance between the first and second feature vectors satisfies a predetermined condition such as, for example, being at or below a threshold Hamming distance. In another embodiment, the determination made at block 518 may include generating a confidence measure of whether the first user account and the second user account are associated with the same entity.

For the purposes of promoting an understanding of the principles of the disclosure, reference has been made to the embodiments illustrated in the drawings, and specific language has been used to describe these embodiments. However, no limitation of the scope of the disclosure is intended by this specific language, and the disclosure should be construed to encompass all embodiments that would normally occur to one of ordinary skill in the art. Descriptions of features or aspects within each embodiment should typically be considered as available for other similar features or aspects in other embodiments unless stated otherwise. The terminology used herein is for the purpose of describing the particular embodiments and is not intended to be limiting of exemplary embodiments of the disclosure. In the description of the embodiments, certain detailed explanations of related art are omitted when it is deemed that they may unnecessarily obscure the essence of the disclosure.

The use of any and all examples, or exemplary language (e.g., "such as") provided herein, is intended merely to better illuminate the invention and does not pose a limitation on the scope of the invention unless otherwise claimed. Numerous modifications and adaptations will be readily apparent to those of ordinary skill in this art without departing from the scope of the invention as defined by the following claims. Therefore, the scope of the invention is defined not by the detailed description of the invention but by the following claims, and all differences within the scope will be construed as being included in the invention.

No item or component is essential to the practice of the invention unless the element is specifically described as "essential" or "critical". It will also be recognized that the terms "comprises," "comprising," "includes," "including," "has," and "having," as used herein, are specifically intended to be read as open-ended terms of art. The use of the terms "a" and "an" and "the" and similar referents in the context of describing the invention (especially in the context of the following claims) are to be construed to cover both the singular and the plural, unless the context clearly indicates otherwise. In addition, it should be understood that although the terms "first," "second," etc. may be used herein to describe various elements, these elements should not be limited by these terms, which are only used to distinguish one element from another. Furthermore, recitation of ranges of values herein are merely intended to serve as a shorthand method of referring individually to each separate value falling within the range, unless otherwise indicated herein, and each separate value is incorporated into the specification as if it were individually recited herein.

What is claimed is:

1. A method for analyzing social network accounts, the method comprising:
    querying, using data processing hardware, a first social network for data about a first user account associated with the first social network;
    receiving, at the data processing hardware, the data about the first user account associated with the first social network;
    storing, by the data processing hardware, the received data in a social graph structure;
    determining, by the data processing hardware, derived characteristics of the first user account based on the data stored in the social graph structure;
    quantifying, by the data processing hardware, the derived characteristics of the first user account;
    determining, by the data processing hardware, a psychological profile for the first user account based on the derived characteristics of the first user account, wherein determining the psychological profile for the first user account comprises:
        generating, by the data processing hardware, a normalized weighted measurement for at least one predefined personality trait based on the derived characteristics of the first user account;
    generating, by the data processing hardware, a first feature vector for the first user account based on the quantified characteristics of the first user account and the normalized weighted measurement for the at least one predefined personality trait;
    comparing, by the data processing hardware, the first feature vector of the first user account with a second feature vector of a second user account associated with a second social network different from the first social network; and
    determining, by the data processing hardware, based on the comparison of the first and second feature vectors, whether the first user account and the second user account are associated with a same entity,
    wherein the first user account and the second user account are determined to be associated with the same entity when the comparison satisfies a predetermined condition.

2. The method of claim 1, wherein the at least one predefined personality trait includes at least one of (i) agreeableness, (ii) conscientiousness, (iii) extraversion, (iv) emotional range, and (v) openness.

3. The method of claim 1, wherein comparing the first feature vector of the first user account with the second feature vector of the second user account comprises:
    calculating, by the data processing hardware, a Hamming distance between the first feature vector and the second feature vector.

4. The method of claim 3, wherein determining whether the first user account and the second user account are associated with the same entity comprises:
    determining, by the data processing hardware, whether the calculated Hamming distance between the first feature vector and the second feature vector satisfies the predetermined condition,
    wherein the predetermined condition is a threshold Hamming distance.

5. The method of claim 1, wherein the derived characteristics of the first user account are determined based on data about interactions between the first user account and the first social network.

6. The method of claim 1, wherein the derived characteristics of the first user account comprise one or more of (i) frequency of posting in the first social network by the first user account, (ii) IP addresses associated with the first user account, (iii) browser types associated with the first user account, and (iv) dialect associated with the first user account.

7. A system comprising:
    data processing hardware; and
    memory hardware in communication with the data processing hardware and storing instructions that when executed on the data processing hardware cause the data processing hardware to perform operations comprising:
        querying a first social network for data about a first user account associated with the first social network;
        receiving the data about the first user account associated with the first social network;
        storing the received data in a social graph structure;
        determining derived characteristics of the first user account based on the data stored in the social graph structure;
        quantifying the derived characteristics of the first user account;
        determining a psychological profile for the first user account based on the derived characteristics of the first user account, wherein determining the psychological profile for the first user account comprises:
            generating a normalized weighted measurement for at least one predefined personality trait based on the derived characteristics of the first user account;
        generating a first feature vector for the first user account based on the quantified characteristics of the first user account and the normalized weighted measurement for the at least one predefined personality trait;

comparing the first feature vector of the first user account with a second feature vector of a second user account associated with a second social network different from the first social network; and determining, based on the comparison of the first and second feature vectors, whether the first user account and the second user account are associated with a same entity, wherein the first user account and the second user account are determined to be associated with the same entity when the comparison satisfies a predetermined condition.

8. The system of claim 7, wherein the at least one predefined personality trait includes at least one of (i) agreeableness, (ii) conscientiousness, (iii) extraversion, (iv) emotional range, and (v) openness.

9. The system of claim 7, wherein comparing the first feature vector of the first user account with the second feature vector of the second user account comprises:

calculating a Hamming distance between the first feature vector and the second feature vector.

10. The system of claim 9, wherein determining whether the first user account and the second user account are associated with the same entity comprises:

determining whether the calculated Hamming distance between the first feature vector and the second feature vector satisfies the predetermined condition, wherein the predetermined condition is a threshold Hamming distance.

11. The system of claim 7, wherein the derived characteristics of the first user account are determined based on data about interactions between the first user account and the first social network.

12. The system of claim 7, wherein the derived characteristics of the first user account comprise one or more of (i) frequency of posting in the first social network by the first user account, (ii) IP addresses associated with the first user account, (iii) browser types associated with the first user account, and (iv) dialect associated with the first user account.

13. The system of claim 7, wherein the social graph structure is formatted with an actor ontology.

14. A non-transitory computer-readable storage medium including instructions that, when executed by at least one processor of a computing device, cause the computing device to perform operations comprising:

querying a first social network for data about a first user account associated with the first social network;

receiving the data about the first user account associated with the first social network;

storing the received data in a social graph structure;

determining derived characteristics of the first user account based on the data stored in the social graph structure;

quantifying the derived characteristics of the first user account;

determining a psychological profile for the first user account based on the derived characteristics of the first user account, wherein determining the psychological profile for the first user account comprises:

generating a normalized weighted measurement for at least one predefined personality trait based on the derived characteristics of the first user account;

generating a first feature vector for the first user account based on the quantified characteristics of the first user account and the normalized weighted measurement for the at least one predefined personality trait;

comparing the first feature vector of the first user account with a second feature vector of a second user account associated with a second social network different from the first social network; and determining, based on the comparison of the first and second feature vectors, whether the first user account and the second user account are associated with a same entity, wherein the first user account and the second user account are determined to be associated with the same entity when the comparison satisfies a predetermined condition.

15. The non-transitory computer-readable storage medium of claim 14, wherein the at least one predefined personality trait includes at least one of (i) agreeableness, (ii) conscientiousness, (iii) extraversion, (iv) emotional range, and (v) openness.

16. The non-transitory computer-readable storage medium of claim 14, wherein comparing the first feature vector of the first user account with the second feature vector of the second user account comprises:

calculating a Hamming distance between the first feature vector and the second feature vector.

17. The non-transitory computer-readable storage medium of claim 16, wherein determining whether the first user account and the second user account are associated with the same entity comprises:

determining whether the calculated Hamming distance between the first feature vector and the second feature vector satisfies the predetermined condition, wherein the predetermined condition is a threshold Hamming distance.

18. The non-transitory computer-readable storage medium of claim 14, wherein the derived characteristics of the first user account are determined based on data about interactions between the first user account and the first social network.

19. The non-transitory computer-readable storage medium of claim 14, wherein the derived characteristics of the first user account comprise one or more of (i) frequency of posting in the first social network by the first user account, (ii) IP addresses associated with the first user account, (iii) browser types associated with the first user account, and (iv) dialect associated with the first user account.

* * * * *